United States Patent
Keinänen et al.

(10) Patent No.: US 8,152,793 B2
(45) Date of Patent: Apr. 10, 2012

(54) MEMBRANE SHELL OF AN IMPLANTABLE DOSAGE SYSTEM

(75) Inventors: Antti Keinänen, Turku (FI); Jukka Koskinen, Tampere (FI); Pentti Järvelä, Lahti (FI)

(73) Assignee: Bayer Oy, Turku (FI)

( * ) Notice: Subject to any disclaimer, the term of this patent is extended or adjusted under 35 U.S.C. 154(b) by 152 days.

(21) Appl. No.: 12/597,679

(22) PCT Filed: Apr. 23, 2008

(86) PCT No.: PCT/FI2008/050217
§ 371 (c)(1),
(2), (4) Date: Oct. 26, 2009

(87) PCT Pub. No.: WO2008/132274
PCT Pub. Date: Nov. 6, 2008

(65) Prior Publication Data
US 2010/0062034 A1    Mar. 11, 2010

(30) Foreign Application Priority Data

Apr. 27, 2007  (FI) .................................. 20070171 U

(51) Int. Cl.
*A61K 9/22* (2006.01)
*A61K 9/02* (2006.01)
*A61M 31/00* (2006.01)
*A61F 13/00* (2006.01)
*A61F 2/00* (2006.01)

(52) U.S. Cl. ............... 604/891.1; 604/890.1; 604/93.01; 604/288; 424/422; 424/424

(58) Field of Classification Search .................. 424/422, 424/424–426; 604/131, 890.1, 891.1, 892.1, 604/93.01
See application file for complete search history.

(56) References Cited

U.S. PATENT DOCUMENTS

| 4,929,233 A * | 5/1990 | Roth et al. ................... 604/131 |
| 6,508,808 B1 * | 1/2003 | Carr et al. ................... 604/892.1 |
| 2006/0233881 A1 | 10/2006 | Sowden |

FOREIGN PATENT DOCUMENTS

| WO | WO-02/053129 A1 | | 7/2002 |
| WO | WO 2006/039459 | * | 4/2006 |
| WO | WO-2006/039459 A1 | | 4/2006 |

* cited by examiner

*Primary Examiner* — Kevin C Sirmons
*Assistant Examiner* — Bradley Thomas, Jr.
(74) *Attorney, Agent, or Firm* — Birch, Stewart, Kolasch & Birch, LLP

(57) ABSTRACT

The membrane shell of an implantable dosage system according to the invention is particularly suitable for subcutaneous applications to release an active agent with steady amounts during a longer period of time. The membrane shell (3) according to the invention comprises a first half (1) and a second half (2), which both halves comprise a continuous closure edge (8, 9), and are adapted to be connected to each other through a closable joint. The closure edges (8, 9) of the halves comprise at least one groove (10) and/or at least one protrusion (11) as continuous or discontinuous, and the membrane shell (3) is adapted to be closed so that at least one protrusion (11) and/or at least one groove (10) of the second half becomes opposed to at least one groove (10) and/or at least one protrusion (11) of the first half through a snap-fit joint.

16 Claims, 2 Drawing Sheets cross-section A-A

MEMBRANE SHELL OF AN IMPLANTABLE DOSAGE SYSTEM

TECHNICAL FIELD

The invention relates to a membrane shell of a dosage system of an active agent, particularly to a membrane shell of a dosage system for subcutaneous application and releasing an active agent with steady amounts during a longer period of time. More particularly, the invention relates to a membrane shell comprising a closable joint. The invention also relates to an implantable dosage system, or an implant, comprising a membrane shell according to the invention and a core or cores embedded therein and containing an active agent.

STATE OF ART

Dosage systems for subcutaneous application and releasing an active agent for a given time period with a given rate, most preferably with a steady rate, or implants, can be roughly divided into four groups.

In matrix-type implants, the active agent is dispersed in a carrier material matrix. The carrier material may be porous or non-porous, solid or semi-solid, and it may permeate the active agent or not. The matrix-type implants may be biodegradable so that they will slowly degrade after the drug delivery has terminated. On the other hand, non-degradable matrix-type implants release the active agent by diffusion through the walls or pores of the matrix. The matrix-type implants are simple to fabricate, but they cannot be employed for delivering certain active agents. The problem with the matrix-type implants is to achieve a steady release rate (zero order kinetics), since the release rate typically depends on the concentration of the active agent in the matrix.

Core-type implants comprise a core/cavity containing the active agent (reservoir) and a membrane surrounding it and controlling the release rate (rate controlling membrane, rcm). The membrane may be porous or non-porous, but usually it is not biodegradable. The release rate of the core-type implants generally remains constant more easily, because the release rate mostly depends only on the surface area of the membrane.

The third group is so-called hybrid implants, which contain a matrix core inside a rate controlling membrane.

Other drug release systems may be mechanical in nature and contain a tiny electronic or osmotic pump filled with a drug. A steady release is easily achieved with this type of devices, but they are very expensive and thus cannot compete with the matrix-type and core-type implants.

Publication GB 1,157,370 discloses an implant for subcutaneous use, which consists of porous (mesh-like) top and bottom layers, a relatively thick inert inner layer for drug pellets, and an annular sidewall. The shells of the implant can be fabricated by e.g. moulding from polyethylene as two separate parts, or as connected to each other through a hinge. This solution features a very complex structure consisting of a number of separate parts, whereby the assembly of the implant becomes very laborious and difficult.

Publication EP 1 100 669 discloses an implantable dosage system fabricated by injection moulding. According to the publication, the shape of the implant can be defined according to the purpose, particularly ring- or rod-shaped implants were mentioned. The core inside the shell or the membrane may be essentially a solution, or it may contain air, or it may be a solution suspension of an active agent, or a powder form of an active agent. In this fabrication technique, the drug is incorporated into the implant during the fabrication of the membrane shell.

In the dosage systems of an active agent for subcutaneous use according to prior art, the quantity and the strength of the active agent in the product need have been determined in most cases already prior to the fabrication of the end product, or in the course of it at the latest. For example, in the core-type solutions, either the core containing the active agent has been incorporated inside the membrane during the fabrication of the membrane shell, or the shell has been generated afterwards on the core by employing e.g. dip coating.

Implants comprising a membrane and based on extrusion technique are usually rod-shaped or ring-shaped, and in them as well, the active agent has been incorporated into the implant either simultaneously with the extrusion of the membrane, or the shell has been generated on the completed core afterwards.

While it is known to fabricate implants with various shapes and sizes with different techniques there has existed a problem that the implants prepared in a specific manner for specific purposes are tightly restricted to a certain model and a certain way of embedding the active agent inside the membrane. It would be advantageous to be able to employ a membrane shell with the same structure/shape for various purposes and e.g. to determine the required composition and strength of the active agent case-specifically according to the application.

BRIEF DESCRIPTION OF THE INVENTION

The invention relates to a membrane shell of an implantable dosage system, comprising a first half and a second half, which both halves comprise an inner surface and an outer surface so that the halves have been adapted to be connected to each other through a closable joint comprising a closure edge of the first half as continuous on the inner surface of the first half, essentially at its outer perimeter, and a closure edge of the second half as continuous on the inner surface of the second half, essentially at its outer perimeter, and which closure edges of the halves comprise at least one groove and/or at least one protrusion as continuous or as discontinuous, and which membrane shell has been adapted to be closed so that at least one protrusion and/or at least one groove of the second half becomes opposed to at least one groove and/or at least one protrusion of the first half through a snap-fit joint.

According to an embodiment, the closure edge of the first half of the membrane shell according to the invention comprises a continuous groove, and the closure edge of the second half comprises a continuous protrusion.

The first half and the second half of the membrane shell according to the invention may be connected to each other through a membrane hinge.

The membrane shell can be fabricated preferably from polydimethyl siloxane of injection moulding quality.

The halves of the membrane shell according to the invention comprise, in addition to the closure edge, at least one cavity pit, or pit, on the inner surface of the first half and/or of the second half, essentially in the middle of it. According to an embodiment, at least one cavity pit of the first half has been adapted to become opposed to at least one cavity pit of the second half upon closing the membrane shell with the inner surfaces against each other.

The invention also relates to an implantable dosage system, or an implant, comprising a membrane shell according to the invention and a core/cores containing an active agent and adapted to be incorporated into at least one cavity inside the membrane shell.

The ready shaped core(s) can be incorporated into the cavity pit(s) of the membrane shell before closing the shell through a snap-fit joint. Alternatively, the core(s) can be injected into at least one cavity inside the closed membrane shell.

The membrane shell according to the present invention, comprising a closable joint, enables the embedding of a drug inside an implant in various ways and in different forms. In this way, e.g. the release of the drug can be influenced. The administration of the active agent into a completed membrane shell enables the determination of the dose, the state and the strength of the agent case-specifically after the fabrication of the actual implant shell. While the thickness and the surface area of the membrane shell affect the release rate of the active agent, it can also be partly influenced by the form in which the active agent is incorporated into the membrane shell.

The injection moulding technique enables free shaping, whereby the shape can be chosen according to the object of therapy.

It is known that active agents do not function with all cross-linking systems. The implant according to the present invention makes possible that the core comprising the active agent may have a cross-linking system different from that of the membrane. Thus, the cross-linking system employed in the membrane shell is not bounded by the cross-linking system that is suitable for the active agent.

DRAWINGS

DETAILED DESCRIPTION OF THE INVENTION

Herein an implant, or a dosage system of an active agent for subcutaneous use, refers to the complex formed by a membrane shell and a core comprising an active agent.

An active or an effective agent refers to an agent suitable for use in implants for humans or animals, e.g. a drug or a hormone providing a desired medicinal or some other kind of effect or impact.

A membrane shell of an implantable dosage system according to the invention is fabricated by injection moulding from a plastic material that is suitable for the purpose of use. Various thermosetting plastics can be applied. Preferred materials are elastomers, such as silicone copolymers. An especially preferred material for use in a membrane shell according to the invention is polydimethyl siloxane, PDMS.

Figure 1A:
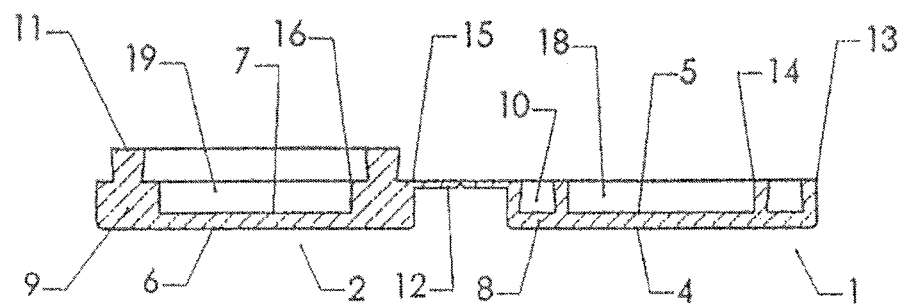
FIG. 1a shows a membrane shell of an implant according to the invention before closing in top view, and its cross-section A-A.
Figure 1A:
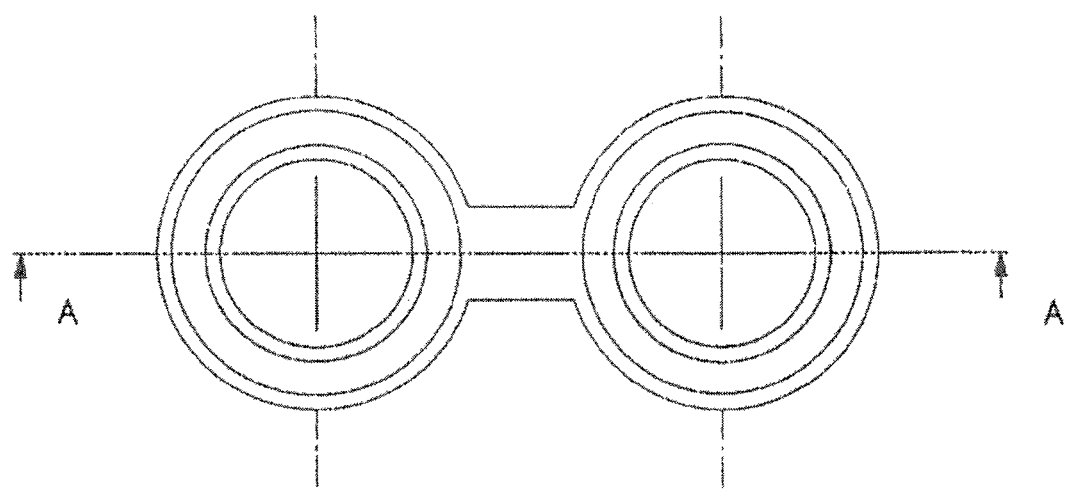
Figure 1B:
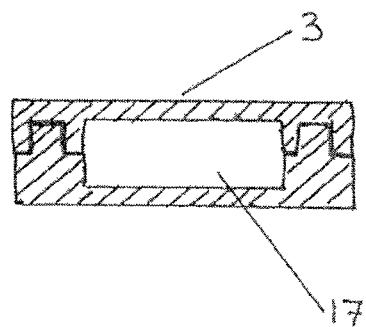
FIG. 1b shows a cross-section of a membrane shell in a closed configuration.

FIGS. 1a and 1b show a membrane shell (3) of an implantable dosage system according to the invention, comprising a first half (1) and a second half (2). An implant fabricated by employing a membrane shell according to FIGS. 1a and 1b is cylinder-shaped so that the horizontal cross-sectional surface of the cylinder is round and the height of the cylinder, i.e. the thickness of the implant, is essentially constant over the entire cross-sectional surface. The halves (1, 2) may be connected to each other through a membrane hinge (12), in this way the different halves will remain better connected, which, among other things, will facilitate the alignment of the halves upon closing the membrane shell, and secondly, it will also facilitate the handling of the tiny objects by keeping the matching parts connected to each other. However, the membrane hinge (12) is not necessary, and it can be removed from the closed membrane shell (3) before setting the implant.

The first half (1) comprises an outer surface (4), which refers to the surface of the first half which is within sight when the membrane shell is in a closed configuration. The outer surface (4) of the first half is limited by an outer edge (13) of the first half, which refers to the point at the edge of the first half at which the first half (1) and the second half (2) contact each other when the shell (3) is in a closed configuration.

The first half also comprises an inner surface (5), which refers to the surface of the first half (1) which remains out of sight inside the membrane shell (3) when the membrane shell is in a closed configuration. The inner surface (5) of the first half (1) is limited by the outer edge (13) of the first half. There is a cavity pit (18) of the first half on the inner surface of the first half, essentially in the middle of it. The pit (18) of the first half forms a first side of a cavity (17) generated inside the membrane shell. The pit of the first half is limited by the inner edge (14) of the first half.

There is a closure edge (8) of the first half on the inner surface (5) of the first half (1), comprising the area extending from the outer edge (13) of the first half to the inner edge (14) of the first half. The width of the closure edge of the first half is equal to the distance from the outer edge (13) to the inner edge (14). In FIG. 1, there is a continuous groove (10) between the outer edge (13) and the inner edge (14) of the first half, or in the area of the closure edge (8) of the first half. The groove (10) of the closure edge (8) of the first half has a certain cross-sectional profile, i.e. a cross-sectional profile of a groove.

Correspondingly, the second half (2) comprises an outer surface (6), which refers to the surface of the second half, which is within sight when the membrane shell is in a closed configuration. The outer surface (6) of the second half is limited by an outer edge (15) of the second half, which refers to the point at the edge of the second half at which the first half (1) and the second half (2) contact each other when the shell is in a closed configuration.

The second half (2) also comprises an inner surface (7), which refers to the surface of the second half which remains out of sight inside the membrane shell (3) when the membrane shell is in a closed configuration. The inner surface (7) of the second half (2) is limited by the outer edge (15) of the second half. There is a cavity pit (19) of the second half on the inner surface (7) of the second half, essentially in the middle of it. The pit (19) of the second half forms a second side of the cavity (17) generated inside the membrane shell (3). The pit (19) of the second half (19) is limited by the inner edge (16) of the second half.

On the inner surface (7) of the second half, there is a closure edge (9) of the second half, comprising the area extending from the outer edge (15) of the second half to the inner edge (16) of the second half. The width of the closure edge of the second half is equal to the distance from the outer edge (15) to the inner edge (16). In FIG. 1, there is a continuous protrusion between the outer edge (15) and the inner edge (16) of the second half, or in the area of the closure edge (9) of the second half. The continuous protrusion (11) of the closure edge (9) of the second half has a certain cross-sectional profile, i.e. a cross-sectional profile of a protrusion.

According to FIG. 1b, the membrane shell (3) and the cavity (17) therein are formed as the first half (1) and the second half (2) are being connected to each other with the inner surfaces against each other through a closable joint. A closable joint, also called a snap-fit joint herein, refers to the complex formed by the continuous closure edge (8) of the first half and the continuous closure edge (9) of the second half. According to an embodiment shown in FIGS. 1a and 1b, the closure of the membrane shell is effected by placing the inner surfaces of the first half and the second half against each other so that the continuous protrusion of the second half becomes opposed to the continuous groove of the first half. With regard to a tight closure of the membrane shell (3) according to the invention, it is essential that the closure edges of the first and the second halves become opposed so that the protrusion becomes tightly placed into the groove.

A closable joint according to the invention, shown in FIGS. 1a and 1b, comprises a continuous closure edge of the first half, which comprises a continuous groove, and a continuous closure edge of the second half which comprises a continuous protrusion. According to the invention, the grooves and the protrusions of the closure edges may have been arranged in other ways as well without departing from the basic inventive concept, i.e. a membrane shell comprising a closable joint. It is also possible that the closure edge comprises, in addition to a groove and/or a protrusion, a flat area without any grooves or protrusions. In the flat area of the closure edge the inner surfaces of the halves become opposed to each other without a snap-fit joint. The proportion and the placement of this flat area within the closure edge should be defined so that the adhesion between the halves will remain sufficient.

For example, the groove of the first half can be discontinuous, whereby the protrusion of the second half will correspondingly be discontinuous so that the grooves of the first half and the protrusions of the second half will become opposed when the inner surfaces of the halves are placed against each other. Discontinuity means herein that the closure edge running along the perimeter of the membrane shell half comprises successively discrete grooves or protrusions of certain length and flat areas between them so that the closure edge becomes a continuous area extending essentially along the entire perimeter of the half.

The closable joint can also be of cogwheel-type, whereby the continuous closure edge of the first half comprises both protrusions and grooves alternately with a certain periodicity. Correspondingly, the continuous closure edge of the second half will comprise grooves and protrusions alternately with a certain periodicity. A closable joint according to the invention is formed as the halves are placed with the inner surfaces against each other so that the protrusions of the first half become placed in the grooves of the second half and, on the other hand, the protrusions of the second half become placed in the grooves of the first half. The number of successive grooves and protrusions in the area of the closure edge can be determined case-specifically.

In the embodiments described above, the protrusions and the grooves were located so that the closure edge comprised a single groove or a single protrusion at a time per unit length in the lateral direction (in FIG. 1, in the area between the inner edge and the outer edge of the half).

According to the invention, it is also possible that the closure edge comprises a plurality of grooves and/or protrusions, e.g. two, side by side in the lateral direction of the closure edge. The grooves and/or the protrusions may run side by side along the entire length of the closure edge or only part of it. The number of side-by-side running grooves and/or protrusions is limited by the facts that, on one hand, the size of the implant cannot be increased infinitely and, on the other hand, sufficient space should be reserved for the core containing the active agent.

In addition to the alternative closure edges described above, also other types of arrangements for protrusions and/or grooves and/or flat zones in the area of the closure edges are conceivable. With regard to the invention, it is essential that the groove(s) and/or the protrusion(s) of the first half of the membrane shell become opposed to the protrusion(s) and/or groove(s) of the second half, resulting in a tight connection of the halves through a snap-fit joint. According to the invention, the closable joint is located essentially at the edge, or at the perimeter, of the half.

FIG. 1 shows the most preferred embodiment of the invention with regard to the closable joint. In this most preferred embodiment, the closable joint comprises a continuous closure edge of the first half comprising a continuous groove, and a continuous closure edge of the second half comprising a continuous protrusion.

The cross-sectional profile of at least one protrusion and groove of the closable joint may be any cross-sectional profile that is suitable for the purpose of use. For example, it may have a so-called dovetail profile, wherein the protrusion (male) is somewhat broadening and the groove (female) is correspondingly broadening towards the bottom of the groove.

The design/sizing of the protrusion and the groove follows principles known to a person skilled in the art, which on one hand relate to the injection moulding technique and on the other hand to the functionality of the closable joint. Due to the injection moulding technique, it must be taken into account e.g. that the protrusion of the second half must become detached of the mould, or the reverse taper (the negative angle) must not be too large. In the design of the closable joint, the most essential is that the halves become connected to each other through the joint.

The term snap-fit joint used herein for the closable joint does not necessarily mean that there should be heard any snapping voice according to the designation of the joint upon connecting the halves to each other when the protrusion becomes opposed to the groove. The principle of the snap-fit joint however best describes the closing mechanism employed in the connection of the halves of the membrane shell according to the invention.

The closable joint according to the invention, the snap-fit joint, is of a unidirectional type, which refers to the fact that the joint is not meant to be opened. If the joint has to be opened later for some reason, e.g. in order to check a possible identification information, it will inevitably result in the failure of the structure of the membrane shell at least to some extent.

According to an embodiment, an agent promoting the adhesion between the halves, such as an adhesive that is suitable for the application, preferably silicone glue, may be applied on the closure edges of the first half and/or the second half.

As is apparent from FIG. 1b, a cavity (17) is formed between the halves upon closing a membrane shell according to FIG. 1a through a closable joint. The cavity pit (18) of the first half forms the first side of the cavity (17), and the cavity pit (19) of the second half forms the second side of the cavity (17). The size and shape of the cavity (17) can be chosen according to the application.

The membrane shell may also be designed so that two or more cavities are formed therein. This kind of embodiment can be employed e.g. if several different active agents are desired to be incorporated inside the same implant.

In the case of two or more cavity pits, the width of the closure edge of the membrane shell half is defined by the distance between the outermost point of the pit located closest to the outer edge of the half, and the outer edge. The outermost point of the pit located closest the outer edge of the half refers to the point of the pit the distance of which from the outer edge of the half is shortest. In the case of multiple cavity pits, the half does not have an actual inner edge, but the width of the closure edge is defined as described above.

The closure edge comprising the area extending from the inner edge (14, 16) of the half to the outer edge (13, 15) of the half must have such a design that the closable joint functions by connecting the halves to each other. The design of the closure edge refers to, among other things, the width of the closure edge (e.g. the distance between the inner edge of the half and the outer edge of the half), the design of the groove and the protrusion (e.g. the cross-sectional profile), and the location of the groove and/or the protrusion in the area of the closure edge in the lateral and longitudinal directions (e.g. one after the other and/or side by side and continuous/discontinuous).

According to an embodiment, the cavity pit(s) can be located in one half only, whereby the inside of the closure edge of the other half is flat. The width of the closure edge of the half lacking a pit is defined according to the width of the closure edge of the half acting as the counterpart. It is also possible that the pits located in separate halves do not become opposed, whereby the cavities become formed into separate halves.

The cavity pit may have any shape, e.g. it may be round-shaped or oval-shaped. It is also possible that the pit(s) run(s) circumferentially in the area limited by the closure edge(s) of the half and/or the halves.

The depth of the cavity pits has to be defined so that the mechanical durability of the implant is sufficient in the application. The thickness of the halves of the membrane shell, or the distance between the inner surface and the outer surface, has to be on the entire area of the half such that the implant will endure without breaking, e.g. collapsing, in the application for the required time.

According to the embodiment shown in FIG. 1, which is the most preferred embodiment with regard to the cavity, the membrane shell comprises one cavity (17), which is formed of the opposing pits (18, 19) of the first and the second halves.

Figure 2A:
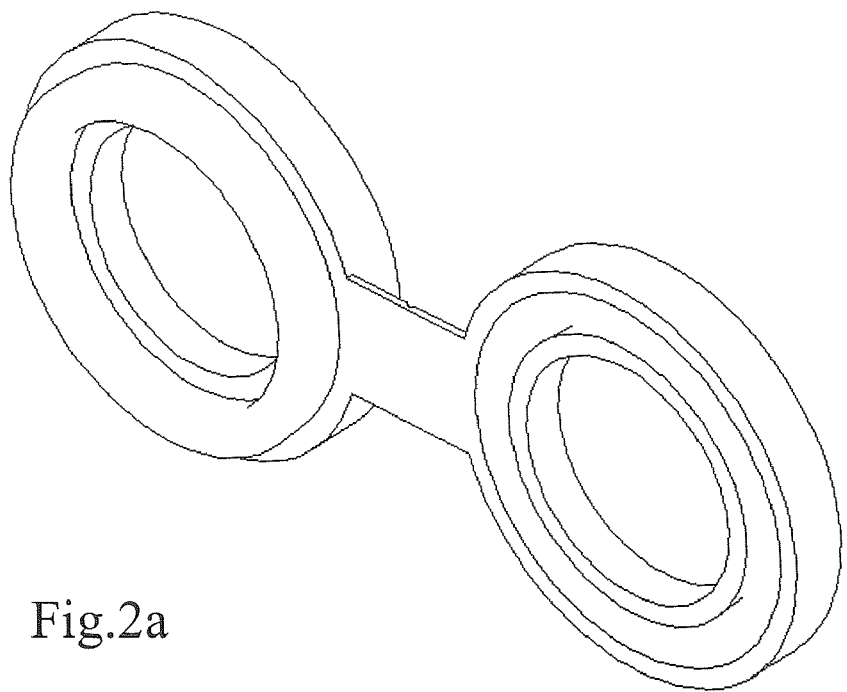
FIG. 2 shows an outline of a membrane shell of an implant according to the invention in an open configuration (FIG. 2a) and in a closed configuration (FIG. 2b).
Figure 2B:
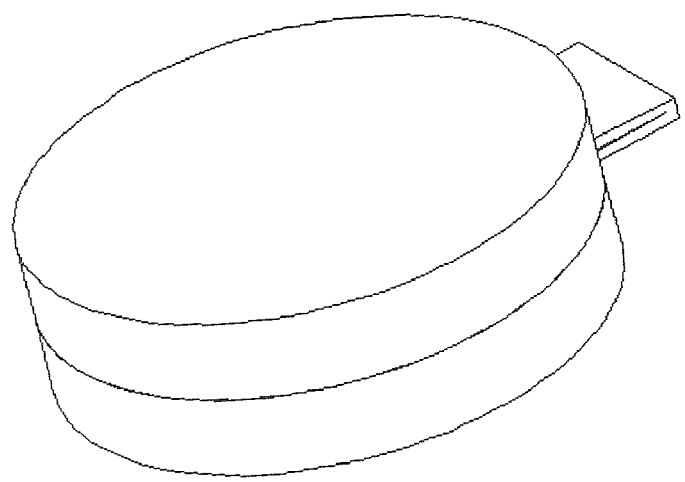

FIG. 2 shows an outline of a membrane shell according to FIG. 1 before and after closure. The figure also shows a membrane hinge.

The shape and design of the membrane shell according to the invention can be chosen freely, which also holds for the appearance of the implant fabricated thereof. The membrane shell according to the invention has to comprise a closable joint located essentially at the edge, and a cavity or cavities remaining between the halves of the membrane shell for placing a core or cores containing an active agent. The appearance of the implant can be chosen according to the object of therapy. A preferred embodiment according to the invention has a cylinder-shaped design so that the horizontal cross-section of the cylinder is essentially round (FIG. 1a) or oval. The height of the cylinder-shaped implant can be essentially constant, or it can be e.g. shallower at the edges. The cylinder-shaped implant with an oval cross-section according to the invention can especially be shallower at the ends of the oval.

The implant may also contain protruding parts with different shapes and designs, e.g. for facilitating adhesion upon removing the implant from the object of therapy. The shape of the protruding part and its location in the implant can be chosen on the basis of the requirements imposed by the purpose of use of the protruding part and/or the application of the implant. The protruding part can be e.g. handle-shaped so that upon removing the implant, a removal hook is placed in the hole of the handle and the implant is pulled out with the help of the hook. In implants for longer-term use, additional protruding parts should be avoided, since the protruding parts may increase scar tissue formation. An essential point with regard to the shape of the implant is the fact that the implant should be as comfortable as possible in its application.

The size, shape and the wall thickness of the membrane shell should be such that the implant will endure in the application for the required time. The lifetime of an implant according to the invention may vary from a few days or weeks to several years. Usually, the lifetime varies from a few months to five years. An implant according to the invention may be employed for the subcutaneous controlled release of an active agent both in humans and in animals.

The design of the membrane shell and correspondingly the overall dimensions of the implant may vary depending on the application. The outer diameter of the implant in an operating situation, or with the membrane shell closed and the core(s) containing an active agent inside the shell, may be e.g. 5-40 mm, preferably it is 5-20 mm, and most preferably it is 10 mm. Particularly an oval-shaped implant may have a length greater than 20 mm, e.g. 40 mm. The height of the implant may be 1-10 mm, generally, it is 1.5-5 mm, and preferably, the height is 2-3 mm. As a limiting factor for the design can be regarded designing the closable joint so that it will enable the implementation by the injection moulding technique and the operation by connecting the halves to each other.

The thickness of the membrane wall and the surface area of the shell contribute to the release rate of the drug, which also has to be taken into account when determining the shape and design of the shell. The release rate of an agent that is effective in ways known to a person skilled in the art can be influenced through surface geometry, such as folds, notches and handles by e.g. increasing the release area for the active agent.

The composition of the membrane shell can be altered by modified PDMS elastomers. For example, the release of the active agent can be influenced through the composition. As an example, it can be noted that if the membrane shell is fabricated from fluorosiloxane, e.g. trifluoropropyl-substituted siloxane, or from a mixture of it and PDMS, the release of the active agent will decelerate, and on the other hand, if the membrane shell is fabricated from a siloxane carrying poly(alkyleneoxide) groups, or from a mixture of it and PDMS, the release of the drug will accelerate.

The release of the drug can also be controlled by the binding matrix of the drug, in addition to the thickness, shape and composition of the membrane shell.

The halves (1, 2) of the membrane shell can be injection moulded separately or as connected to each other through the membrane hinge (12). The membrane hinge can be removed from the implant after connecting the halves. With regard to a closable joint according to the invention, the hinge keeps the separate halves appropriately connected, whereby the closure can be effected easily.

A desired marking, e.g. identification information, can be fabricated on the inner surface of the membrane shell during injection moulding by engraving a text to the mould so that it will be reproduced on the inner surface of the shell. The marking can also be made by e.g. laser to the inner surface of the membrane shell after injection moulding. By these methods, the confidential identification information can be hidden.

The core of the implant containing an active agent can be incorporated into the cavity (17) before or after closing the shell, preferably before closing the shell.

The active agent, which may be e.g. a drug, can be incorporated into the cavity or cavities formed inside the membrane in various ways. In addition, either the core containing the active agent may be of matrix-type, or the active agent may reside in the core without any matrix. An implant comprising a closable joint according to the invention may thus be the hybrid type (a matrix core and a membrane shell controlling the release rate of an active agent) or the core type (a core comprising an active agent and a membrane shell controlling its release rate). In both cases, the core(s) should essentially fill the cavity or the cavities formed inside the membrane shell. Preferably, the resilience of the membrane shell material contributes to the filling of the cavity by the core. An empty space between the core and the cavity is not desirable with regard to the diffusion of the active agent.

The active agent may be e.g. bound to a PDMS elastomer, of which a plate is formed by cross-linking. A disc is cut from the plate and placed inside the membrane shell, and the shell is closed through a snap-fit joint. Alternatively, polyethylene glycol (PEG) may be first injected on the inner surface of the membrane shell, after which the disc is placed inside the shell and the shell is closed. Injecting polyethylene glycol on the inner surface of the membrane shell will improve the contact between the core and the shell.

The core containing an active agent and to be placed in the cavity of the membrane shell can be injection moulded from a PDMS elastomer to which the drug has been bound. After placing the core, the shell is closed through a snap-fit joint.

The drug can be bound to crystalline polyethylene glycol in room temperature. A piece is moulded from the mass and placed inside the membrane shell. Once placed inside the body, PEG will melt and alter the diffusion of the drug. By adjusting the melting point of PEG, melting can be induced as the body temperature rises above normal.

It is also possible to inject an active agent bound to liquid polyethylene glycol or silicone oil in room temperature inside a closed membrane shell.

A separate membrane shell enables having a different cross-linking system in the elastomer containing the drug from that of the membrane shell.

It is also possible that a plate is compressed from an active agent together with a binder, from which plate discs will be cut then. The disc is placed in a cavity pit, and the shell is closed through a snap-fit joint. In this embodiment, the drug is not bound by a matrix.

Irrespective of the number and shape of the cavities, all methods for adding and incorporating an active agent described above are conceivable.

EXAMPLES

Example 1

Fabrication of a Membrane Shell

PDMS elastomer of injection moulding quality, liquid silicone rubber (LSR), in parts A and B are mixed in a volumetric ratio 1:1. Part A contains a platinum catalyst and part B contains a cross-linking agent, thus providing a cross-linkable elastomer. The LSR elastomer is injection moulded to a mould and allowed to cross-link for e.g. 5 minutes at 115° C. Then the membrane shell is removed from the mould.
Fabrication of a Drug Core:

PDMS elastomer and the drug are mixed e.g. in a weight ratio 1:1. The mass is compressed with a hydraulic press for e.g. five minutes at 115° C. A disc/button is cut from a thin plate by a hole press.
Assembly of an Implant:

The core disc containing the drug is placed in one of the membrane shell halves, and the shell is closed by placing the inner surfaces of the halves against each other through a snap-fit joint. Room temperature vulcanising (RTV) siloxane glue can be applied to a closure edge upon closing the membrane shell.

The invention claimed is:

1. A membrane shell of an implantable dosage system incorporating an active agent, comprising:
a first half and
a second half, wherein both the first and second halves comprise an inner surface and an outer surface,
wherein the first and second halves are adapted to be connected to each other through a closable joint comprising a closure edge of the first half as continuous on the inner surface of the first half essentially at a perimeter of the first half and a closure edge of the second half as continuous on the inner surface of the second half essentially at a perimeter of the second half, and the closure edges of the first and second halves comprise at least one groove and/or at least one protrusion as continuous or discontinuous,
wherein the membrane shell is adapted to be closed so that at least one protrusion and/or at least one groove of the second half becomes opposed to at least one groove and/or at least one protrusion of the first half through a snap-fit joint,
wherein the active agent is released through the membrane shell when implanted in a patient, and
wherein the membrane shell is fabricated solely from a molded composition comprising modified PDMS (polydimethyl siloxane) either alone or in combination with PDMS so as to influence the release of the active agent.

2. The membrane shell according to claim 1, wherein the modified PDMS is trifluoropropyl-substituted siloxane or a siloxane carrying poly(alkyleneoxide) groups.

3. The membrane shell according to claim 1 or 2, wherein the closure edge of the first half comprises at least one continuous groove, and the closure edge of the second half comprises at least one continuous protrusion.

4. The membrane shell according to claim 1 or 2, wherein the first half and the second half are connected to each other through a membrane hinge.

5. The membrane shell according to 1 or 2, wherein the membrane shell comprises a cavity pit on the inner surface of the first half and/or of the second half, essentially in the middle of the membrane shell so that the cavity pits of the first half and of the second half are adapted to become opposed upon closing the membrane shell.

6. The membrane shell according to 1 or 2, wherein the membrane shell comprises two or more cavity pits on the inner surfaces of the first half and/or the second half.

7. The membrane shell according to claim 6, wherein the cavity pits of the first half and the second half are adapted to become opposed upon closing the membrane shell.

8. An implant, comprising:
a membrane shell according to claim 1 or 2, and
at least one core containing an active agent, which core is adapted to be incorporated into at least one cavity inside the membrane shell.

9. The implant according to claim 8, wherein at least one ready shaped core is adapted to be placed in at least one cavity pit before closing the shell through a snap-fit joint.

10. The implant according to claim 8, wherein the implant comprises at least one injected core in at least one cavity inside the closed membrane shell.

11. A membrane shell of an implantable dosage system incorporating an active agent, comprising:
a first half and a second half, wherein both the first and second halves comprise an inner surface and an outer surface, wherein the first and second halves are adapted to be connected to each other through a closable joint comprising a closure edge of the first half as continuous on the inner surface of the first half essentially at a perimeter of the first half and a closure edge of the second half as continuous on the inner surface of the second half essentially at a perimeter of the second half, and the closure edges of the first and second halves comprise at least one groove and/or at least one protrusion as continuous or discontinuous, wherein the membrane shell is adapted to be closed so that at least one protrusion and/or at least one groove of the second half becomes opposed to at least one groove and/or at least one protrusion of the first half through a snap-fit joint, wherein the active agent is released through the membrane shell when implanted in a patient, and wherein the membrane shell is fabricated from modified PDMS (polydimethyl siloxane) either alone or in combination with PDMS so as to influence the release of the active agent.

12. The membrane shell according to claim 11, wherein the modified PDMS is trifluoropropyl-substituted siloxane or a siloxane carrying poly(alkyleneoxide) groups.

13. The membrane shell according to claim 11, wherein the closure edge of the first half comprises at least one continuous groove, and the closure edge of the second half comprises at least one continuous protrusion.

14. The membrane shell according to claim 11, wherein the first half and the second half are connected to each other through a membrane hinge.

15. An implant comprising:
a membrane shell, comprising
　　a first half and a second half, wherein both the first and second halves comprise an inner surface and an outer surface,
　　wherein the first and second halves are adapted to be connected to each other through a closable joint comprising a closure edge of the first half as continuous on the inner surface of the first half essentially at a perimeter of the first half and a closure edge of the second half as continuous on the inner surface of the second half essentially at a perimeter of the second half, and the closure edges of the first and second halves comprise at least one groove and/or at least one protrusion as continuous or discontinuous,
　　wherein the membrane shell is adapted to be closed so that at least one protrusion and/or at least one groove of the second half becomes opposed to at least one groove and/or at least one protrusion of the first half through a snap-fit joint,
　　wherein the membrane shell is fabricated solely from a molded composition comprising modified PDMS (polydimethyl siloxane) either alone or in combination with PDMS so as to influence the release of the active agent; and
at least one core containing an active ingredient, which core is incorporated into at least one cavity inside the membrane shell, wherein the active ingredient is released through the membrane shell when the implant is implanted in a patient.

16. The implant of claim 15, wherein the modified PDMS is trifluoropropyl-substituted siloxane or a siloxane carrying poly(alkyleneoxide) groups.

* * * * *